US008455685B2

(12) United States Patent
Scates

(10) Patent No.: US 8,455,685 B2
(45) **Date of Patent: *Jun. 4, 2013**

(54) ACETIC ANHYDRIDE PRODUCTION BY WAY OF CARBONYLATION WITH ENHANCED REACTION AND FLASHING

(75) Inventor: Mark O. Scates, Houston, TX (US)

(73) Assignee: Celanese International Corporation, Irving, TX (US)

(*) Notice: Subject to any disclaimer, the term of this patent is extended or adjusted under 35 U.S.C. 154(b) by 339 days.

This patent is subject to a terminal disclaimer.

(21) Appl. No.: 12/924,429

(22) Filed: Sep. 27, 2010

(65) Prior Publication Data

US 2011/0021816 A1 Jan. 27, 2011

Related U.S. Application Data

(63) Continuation-in-part of application No. 12/459,725, filed on Jul. 7, 2009, now Pat. No. 8,168,822.

(51) Int. Cl.
*C07C 51/12* (2006.01)

(52) U.S. Cl.
USPC .......... 562/891; 562/519

(58) Field of Classification Search
None
See application file for complete search history.

(56) References Cited

U.S. PATENT DOCUMENTS

| | | | | |
|---|---|---|---|---|
| 5,001,259 | A | 3/1991 | Smith et al. | 562/519 |
| 5,026,908 | A | 6/1991 | Smith et al. | 562/519 |
| 5,144,068 | A | 9/1992 | Smith et al. | 562/519 |
| 5,416,237 | A | 5/1995 | Aubigne et al. | 562/519 |
| 5,529,970 | A | 6/1996 | Peng | 502/400 |
| 5,696,284 | A | 12/1997 | Baker et al. | 560/232 |
| 5,770,768 | A | 6/1998 | Denis et al. | 562/519 |
| 5,877,347 | A | 3/1999 | Ditzel et al. | 562/519 |
| 5,877,348 | A | 3/1999 | Ditzel et al. | 562/519 |
| 5,883,295 | A | 3/1999 | Sunley et al. | 562/519 |
| 5,932,764 | A | 8/1999 | Morris et al. | 562/519 |
| 5,942,460 | A | 8/1999 | Garland et al. | 502/150 |
| 6,322,612 | B1 | 11/2001 | Sircar et al. | 95/97 |
| 6,627,770 | B1 | 9/2003 | Cheung et al. | 562/519 |
| 6,657,078 | B2 | 12/2003 | Scates et al. | 562/519 |
| 8,168,822 | B2 * | 5/2012 | Scates | 562/519 |
| 2009/0156859 | A1 * | 6/2009 | Scates et al. | 562/517 |

FOREIGN PATENT DOCUMENTS

| | | |
|---|---|---|
| CN | ZL92108244.4 | 6/1999 |
| CN | ZL 94100505.4 | 6/2000 |
| CN | 1345631 | 4/2002 |
| CN | 1349855 | 5/2002 |
| CN | 1651388 | 7/2007 |
| EP | 0 161 874 A1 | 11/1985 |
| EP | 0 759 419 A1 | 2/1997 |
| EP | 0 849 248 A1 | 6/1998 |

OTHER PUBLICATIONS

"Process of 200ktpa Methanol Low Press Oxo Synthesis AA" (SWRDICI 2006) (China).

* cited by examiner

*Primary Examiner* — Yevegeny Valenrod
(74) *Attorney, Agent, or Firm* — Michael W. Ferrell

(57) ABSTRACT

A method of making acetic anhydride or a mixture of acetic anhydride and acetic acid comprising: (a) catalytically reacting a feedstock containing methyl acetate and/or dimethyl ether with carbon monoxide in the presence of a homogeneous rhodium catalyst and methyl iodide in a reactor vessel which contains a substantially anhydrous liquid reaction mixture including acetic acid, acetic anhydride, methyl acetate and/or dimethyl ether, methyl iodide and the homogeneous catalyst, the reactor vessel being operated at a reactor pressure; (b) withdrawing reaction mixture from the reaction vessel and feeding the withdrawn reaction mixture along with additional carbon monoxide to a pre-flasher/post reactor vessel operated at a reduced pressure below the reactor vessel pressure; (c) venting light ends in the pre-flasher vessel and concurrently consuming methyl acetate and/or dimethyl ether in the pre-flasher/post reactor vessel to produce a pre-flash mixture which is enriched in acetic anhydride and diminished in methyl iodide and methyl acetate and/or dimethyl ether as compared with the reaction mixture; (d) withdrawing the pre-flash reaction mixture from the pre-flasher/post reactor vessel and feeding the pre-flash mixture to a flash vessel; and (e) flashing a crude product stream from the mixture in a flash vessel operated at a pressure substantially below the pressure of the pre-flasher/post reactor vessel.

20 Claims, 2 Drawing Sheets

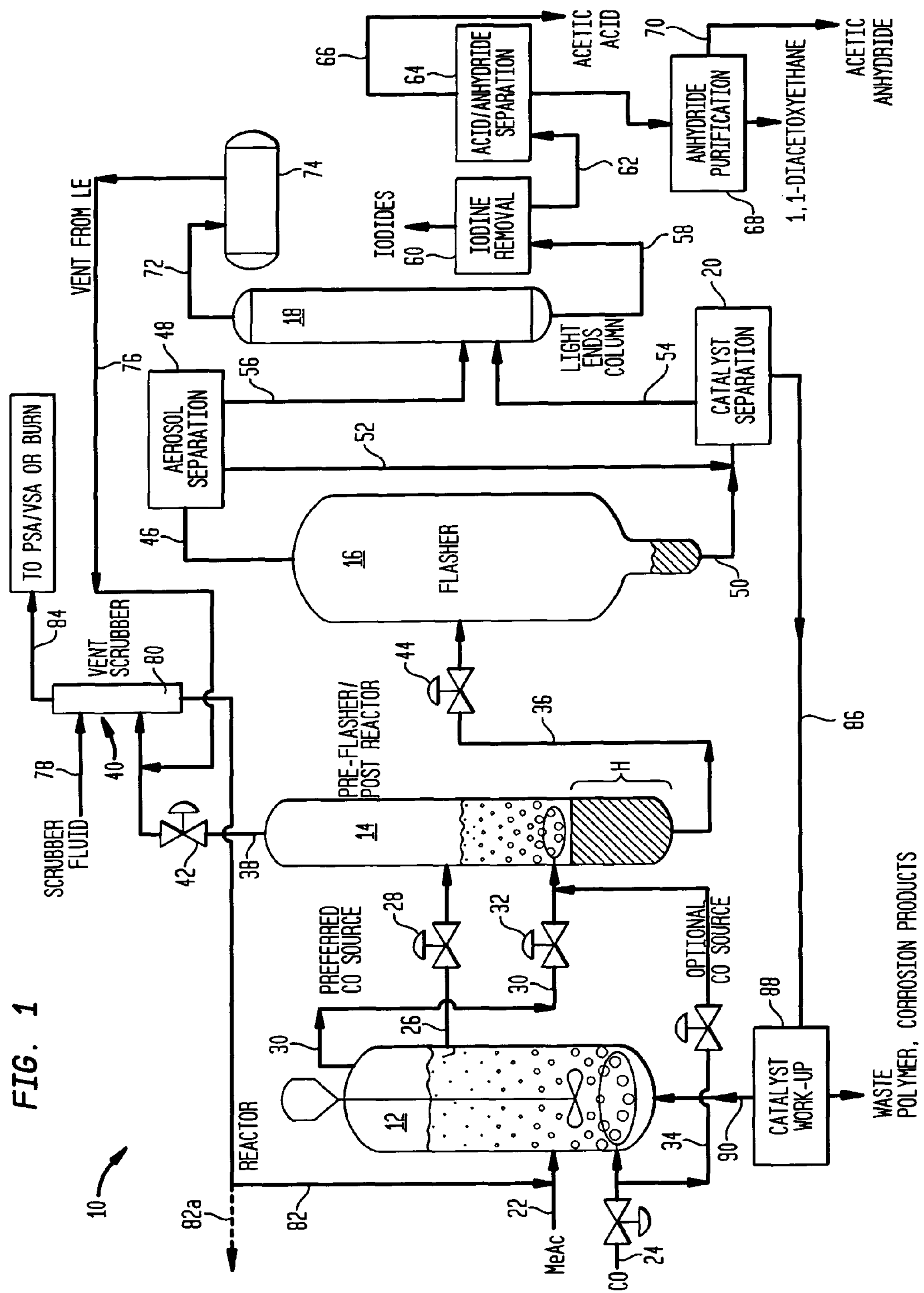
FIG. 1
10
REACTOR
12
MeAc
CO
22
24
26
28
30
32
34
36
38
40
42
44
46
48
50
52
54
56
58
60
62
64
66
68
70
72
74
76
78
80
82
82a
84
86
88
90
PREFERRED CO SOURCE
OPTIONAL CO SOURCE
PRE-FLASHER/ POST REACTOR
14
H
FLASHER
16
AEROSOL SEPARATION
CATALYST SEPARATION
20
LIGHT ENDS COLUMN
18
IODINE REMOVAL
IODIDES
ACID/ANHYDRIDE SEPARATION
ACETIC ACID
ANHYDRIDE PURIFICATION
ACETIC ANHYDRIDE
1,1-DIACETOXYETHANE
VENT FROM LE
VENT SCRUBBER
SCRUBBER FLUID
TO PSA/VSA OR BURN
CATALYST WORK-UP
WASTE POLYMER, CORROSION PRODUCTS

ACETIC ANHYDRIDE PRODUCTION BY WAY OF CARBONYLATION WITH ENHANCED REACTION AND FLASHING

CROSS REFERENCE TO RELATED APPLICATION

This application is a continuation-in-part of U.S. patent application Ser. No. 12/459,725, filed Jul. 7, 2009, entitled "Acetic Acid Production by Way of Carbonylation With Enhanced Reaction and Flashing", now U.S Pat. No. 8,168,822, the disclosure of which is incorporated herein by reference.

TECHNICAL FIELD

The present invention relates to acetic anhydride production or coproduction of acetic acid and acetic anhydride. There is provided a carbonylation system having an intermediate pressure, pre-flash/post reactor vessel that removes methyl iodide and consumes methyl acetate or dimethyl ether prior to flashing in a low pressure flasher. A scrubber/absorber system debottlenecks the light ends column of the purification train.

BACKGROUND OF THE INVENTION

The preparation of acetic anhydride by contacting in the liquid phase a mixture comprising methyl acetate and/or dimethyl ether and methyl iodide with carbon monoxide in the presence of a carbonylation catalyst at elevated pressures and temperatures has been reported extensively in the patent literature. See, for example, U.S. Pat. Nos. 3,927,078; 4,046,807; 4,115,444; 4,252,741; 4,334,884; 4,374,070; 4,430,273; 4,559,183; 5,003,104; 5,292,948 and 5,922,911 and European Patents 8396; 87,869; and 87,870. These patents disclose that the reaction rate can be increased if the catalyst system includes a promoter such as certain amines and quaternary ammonium compounds, phosphines and phosphonium compounds and/or inorganic compounds such as alkali metal salts, e.g., lithium iodide. Normally, both the reaction (process) mixture and the crude product are substantially anhydrous, homogeneous liquids comprising a solution of the reactants and catalyst components in an inert solvent such as acetic acid. Thus, the crude, liquid product obtained from such acetic anhydride processes typically comprises a mixture of acetic anhydride and acetic acid as a result of the use of acetic acid as a process solvent.

Acetic acid may be coproduced in the process by feeding methanol and/or water to the production system, e.g., by feeding methanol and/or water to a process recycle stream containing acetic anhydride and/or to the carbonylation reactor. See, for example, U.S. Pat. No. 5,380,929, U.S. Pat. No. 6,130,355, EP-00087869-B1 and EP-00087870-B1. U.S. Pat. No. 4,374,070 discloses adding methanol to an acetic anhydride-containing recycle stream.

Generally speaking, an acetic anhydride production line or a co-production line includes a reaction section, a purification section, light ends recovery and a catalyst recovery system. In the reaction section, methyl acetate and/or dimethyl ether, methyl iodide and carbon monoxide are contacted with a Group VIII metal catalyst such as a rhodium catalyst in a homogenous stirred liquid phase reaction medium in a reactor. The reaction section also generally includes a flash vessel coupled to the reactor which flashes a draw stream in order to remove crude product from the reaction section. The crude product is fed to a purification section which includes generally a light ends or stripper column, iodine removal, and auxiliary separation/purification, as discussed hereinafter. In the process, various non-condensible vent streams containing light ends, notably methyl iodide, carbon monoxide and methyl acetate are generated and fed to the light ends recovery section. These vent streams are scrubbed with a solvent to remove the light ends which are returned to the system or discarded.

There is an ongoing need for better energy and raw material efficiency as is seen, for example, in United States Patent Application Publication No. US 2007/0287862 of Kline et al. entitled "Production of Acetic Acid and Mixtures of Acetic Acid and Acetic Anhydride". This reference discloses a process for the production of acetic acid or mixtures of acetic acid and acetic anhydride in a carbonylation process wherein a mixture comprising methyl acetate and/or dimethyl ether and methyl iodide is contacted in the liquid phase with carbon monoxide in the presence of a carbonylation catalyst at elevated pressures and temperatures. Methanol, water, or a mixture thereof is added to an acetic anhydride-containing stream within a flash evaporation zone to convert some or all of the acetic anhydride to acetic acid and optionally methyl acetate and to provide heat for the evaporation of a portion of the product effluent produced by the carbonylation process.

In accordance with the present invention, there is provided an improved carbonylation system with staged reaction and pre-flash removal of light ends to increase productivity and purification efficiencies.

SUMMARY OF THE INVENTION

There is provided a system and a method of making acetic anhydride or a mixture of acetic anhydride and acetic acid including (a) catalytically reacting a feedstock containing methyl acetate and/or dimethyl ether with carbon monoxide in the presence of a homogeneous rhodium catalyst and methyl iodide in a reactor vessel which contains a substantially anhydrous liquid reaction mixture including acetic acid, acetic anhydride, methyl acetate and/or dimethyl ether, methyl iodide and the homogeneous catalyst, the reactor vessel being operated at a reactor pressure; (b) withdrawing reaction mixture from the reaction vessel and feeding the withdrawn reaction mixture along with additional carbon monoxide to a pre-flasher/post reactor vessel operated at a reduced pressure below the reactor vessel pressure; and (c) venting light ends in the pre-flasher vessel and concurrently consuming methyl acetate and/or dimethyl ether in the pre-flasher/post reactor vessel to produce a pre-flash mixture which is enriched in acetic anhydride and diminished in methyl iodide and methyl acetate and/or dimethyl ether as compared with the reaction mixture. The process further includes (d) withdrawing the pre-flash reaction mixture from the pre-flasher/post reactor vessel and feeding the pre-flash mixture to a flash vessel; (e) flashing a crude product stream from the mixture in a flash vessel operated at a pressure substantially below the pressure of the pre-flasher/post reactor vessel; (f) recycling post-flash residue from the flash vessel to the reactor vessel; and (g) purifying the crude product stream.

Advantages of the inventive system include increased productivity, debottlenecking of the light ends column and optionally increased carbon monoxide efficiency as well as enhanced catalyst stability.

The pre-flasher/post reactor vessel is suitably operated at a pressure of at least 5 or 10 psi lower than the pressure of the reaction vessel, preferably at least 15 psi lower than the pressure of the reactor vessel. In some embodiments the preflasher/post reactor vessel is operated at a pressure of at least 20 psi, 25 psi or 30 psi lower than the pressure of the reactor vessel.

Supplemental sparging of carbon monoxide from a reactor vent to the pre-flasher/post reactor vessel in order to consume methyl acetate or dimethyl ether is preferred.

Further details and advantages of the present invention will become apparent from the discussion which follows.

BRIEF DESCRIPTION OF THE DRAWINGS

The invention is described in detail below with reference to the appended drawings, wherein like numerals designate similar parts and wherein:

FIG. 1 is a schematic diagram illustrating a carbonylation system for making acetic anhydride or co-producing acetic acid and acetic anhydride in accordance with the invention.

DETAILED DESCRIPTION OF THE INVENTION

Figure 2:
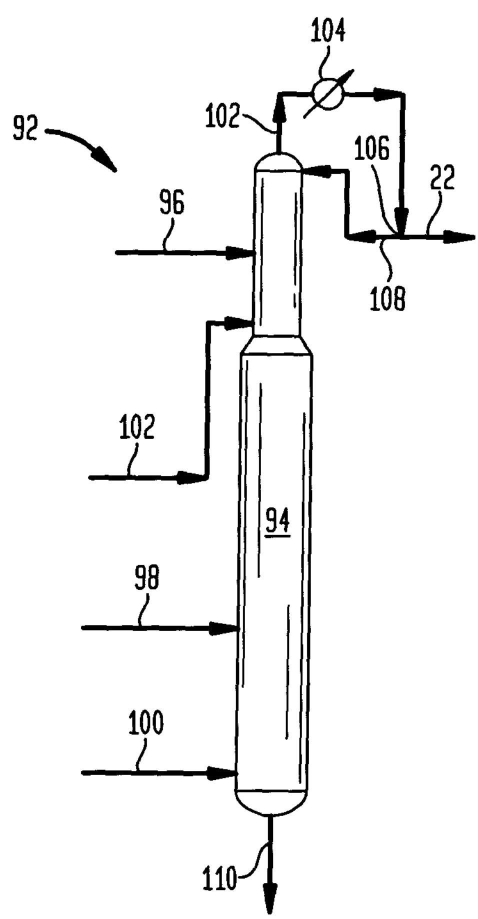
FIG. 2 is a schematic diagram illustrating an esterification tower optionally coupled to the absorber/scrubber unit and the reactor.

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. Percent, % and like terms refer to weight percent, unless otherwise indicated.

A "substantially anhydrous liquid reaction mixture" and like terminology refers to a reaction mixture with essentially no available water, i.e., less than a finite amount.

A homogeneous catalyst system refers generally to a catalytic system wherein a catalytic metal, usually as part of an organometallic complex such as an organic rhodium complex is molecularly dispersed in the same phase with reactants, typically in a solvent medium. See *Applied Homogeneous Catalysis With Organometallic Compounds*, Cornils, B. and Herrmann, W., Ed. Bench Edition, Wiley (Weinheim 2000), Chapter 2, the disclosure of which is incorporated herein by reference.

An " iodide salt stabilizer/co-promoter" and like terminology refers to components which generate and maintain elevated levels of iodide anions, that is, over and above levels attributable to hydriodic acid. The iodide salt stabilizer/co-promoter may be a simple salt or any compound or component that generates and maintains iodide anion in the reaction mixture as is further discussed herein.

"Light ends" refers to components having a boiling point lower than acetic anhydride and acetic acid. Thus, methyl iodide, methyl acetate, dimethyl ether and dissolved carbon monoxide are "light ends" for present purposes.

"Low pressure" and like terminology refers to pressures lower than the pressure maintained in a carbonylation reactor of the class discussed herein. A "reduced" pressure is usually at least 5 psi lower than a referenced pressure, preferably at least 10 psi or 20 psi lower than a referenced pressure. A "low pressure" absorber refers to an absorber operated at a pressure substantially lower than the reactor pressure, preferably more than 25 psi lower than the pressure maintained in the carbonylation reactor.

"Non-condensables" and like terminology refers to gaseous material not liquefied when associated water vapor and/or other vapors are condensed in the same environment, for example, carbon monoxide is a noncondensable. In most cases, non-condensibles refers to materials which are not liquid, except under cryogenic conditions, i.e. fixed gasses.

When referring to a reduction in methyl acetate or dimethyl ether due to consumption and removal thereof in the pre-flasher/post reactor vessel at specific levels, the percentage reduction is relative to the amount of methyl acetate and/or dimethyl ether in the reaction mixture in the reactor. Thus, a 25% reduction of methyl acetate and/or dimethyl ether or mixtures thereof in the pre-flasher/post reactor refers to a level 25 wt. % lower in the outlet stream of the pre-flasher/post reactor as compared to the level maintained in the reactor vessel. Thus, when the level of methyl acetate and/or dimethyl ether is 4 wt. % in the reactor vessel and methyl acetate and/or dimethyl ether is consumed in the pre-flasher/post reactor vessel to a level of 3%, a 25% reduction is achieved. In some preferred aspects of the invention, methyl acetate and/or dimethyl ether is consumed to a level of less than 1.5 wt. % or less than 1 wt. % in the reaction mixture exiting the pre-flasher/post reactor. In still other cases, the concentration of methyl acetate or dimethyl ether in the stream exiting the pre-flasher/post reactor may be less than 0.5 wt. % or less than 0.25 wt. %

In a conventional carbonylation reactor, vent gas comprising hydrogen, methane, carbon dioxide, and carbon monoxide is fed from the reactor to a high-pressure absorber operated at pressures similar to those in the reactor to recover reactants and/or product. Product is separated from a catalyst solution in a flasher. Methyl iodide, methyl acetate and/or dimethyl ether accompanying the crude product is removed in a light ends column and condensed or scrubbed out of vent gas with an absorber.

In the process according to the invention, vent gas from a primary reactor may be fed directly to a pre-flasher/post reactor vessel, thereby conserving carbon monoxide reactant while reducing or eliminating the need for a high-pressure absorber. Additional carbon monoxide provided to the reaction mixture stabilizes the catalyst and reacts with methyl acetate and/or dimethyl ether to increase productivity of the system.

The pre-flasher/post reactor vessel is operated at a pressure intermediate between the operating pressures of the primary reactor and a subsequent flasher, thereby retaining most of the product in solution, while flashing off methyl iodide, methyl acetate and/or dimethyl ether. The methyl iodide, methyl acetate and/or dimethyl ether flashed off from the pre-flasher/post reactor vessel may be fed to a condenser or may be sent directly to a low-pressure absorber, thereby reducing the load on a subsequent light-ends column. Operation of an absorber is generally more expensive than operation of condensing unit. Therefore, minimizing the need for absorption results in a reduction of operating costs.

The reaction liquid is typically drawn from the reactor and flashed in a staged or multi-step process using a pre-flasher/post reactor vessel as well as a traditional flash vessel as hereinafter described. The crude vapor process stream from the flasher is sent to a purification section which generally includes at least a light ends column as is known in the art, and preferably includes separation and purification equipment to purify the acetic anhydride product.

The present invention is further appreciated by reference to the accompanying FIG. 1 which is a schematic diagram illustrating a typical carbonylation process and apparatus according to an embodiment of the invention.

There is shown in FIG. 1 a carbonylation apparatus 10 constructed in accordance with the present invention. Apparatus 10 includes, generally, a carbonylation reactor 12, a pre-flasher/post reactor vessel 14, a flasher 16, as well as additional purification such as a light ends stripper column 18, a catalyst separation unit 20 and so forth as will be appreciated by one of skill in the art.

In operation, a carbonylatable feedstock such as methyl acetate, dimethyl ether and mixtures thereof optionally containing water and/or methanol and carbon monoxide are fed to reactor vessel 12 by way of lines 22, 24 respectively for reaction in the catalytic reaction medium contained in reactor 12. The carbonylation reaction proceeds in a homogeneous, substantially anhydrous catalytic reaction medium comprising a reaction solvent (typically acetic acid and/or acetic anhydride), acetic anhydride, methyl acetate and/or dimethyl ether, methyl iodide and a homogeneous Group VIII metal catalyst, such as a rhodium catalyst. Optionally included are iodide salts and stabilizers as discussed herein.

From reactor 12, a portion of the reaction medium is fed forward via line 26 through a pressure-reducing value 28 to pre-flasher/post reactor 14. There is also provided via line 30, carbon monoxide by way of vent from reaction vessel 12 to pre-flasher 14 as shown. A preferred source of CO is from vent 30 through a pressure-reducing valve 32 inasmuch as this reduces the need to supply additional fresh carbon monoxide to pre-flasher/post reactor 14 which may be accomplished, for example, via line 34 as shown toward the lower portion of the diagram. Note that carbon monoxide is sparged into vessel 14 at a disengaging height H above the bottom of vessel 14 and line 36 in order to prevent (or reduce the amount of) carbon monoxide from being drawn into line 36. Height H may be at least 0.25 meter or more, preferably at least 0.5 meter, or at least 1 meter.

In pre-flasher/post reactor 14 the reaction medium is held at intermediate pressure while the CO interacts with the reaction mixture and consumes methyl acetate and/or dimethyl ether. In a preferred embodiment, the amount of carbon monoxide added to vessel 14 and the reaction conditions are controlled such that the methyl acetate in the reaction mixture is substantially consumed prior to further processing. Pre-flasher/post reactor 14 is provided with a vent at 38 to remove gases from the system including noncondensibles as well as methyl iodide and optionally some methyl acetate to low pressure scrubbing system 40 as indicated in the diagram. Prior to feeding to the low pressure absorber/scrubber system 40, the pressure in the vent stream 38 is lowered by passing the stream through a pressure-reducing valve indicated at 42.

The reaction mixture is thus modified and pre-conditioned prior to flashing. In particular, a portion of the methyl iodide and optionally a portion of methyl acetate and/or dimethyl ether are removed from the reaction mixture and provided to the low pressure vent scrubbing system prior to flashing at low pressure. In this way, purification requirements for the crude product will be reduced as will be appreciated from the discussion which follows. Following reaction in the pre-flasher/post reactor vessel 14, the conditioned reaction mixture, now depleted of light ends, is fed forward via line 36 through a pressure-reducing valve 44 to flasher 16. In flasher 16, the pressure is reduced with respect to pre-flasher 14 which in turn is reduced with respect to the reactor 12. In flasher 16, crude acetic anhydride and optionally acetic acid is flashed from the reaction mixture and exits as overhead indicated at 46 and is supplied to a light ends column 18 as is known in the art.

An aerosol separation unit 48 may be provided to remove entrained liquid from the product stream which, in turn, is combined with the residue stream 50 from flasher 16 via line 52 as shown.

The flasher residue 50, including catalyst, along with the liquid recovered from line 52 is provided to catalyst separation unit 20 which may include an evaporator to separate additional crude product which exits the unit via line 54.

Crude product is provided to light ends column 18, via lines 54, 56 from the flasher 16 and catalyst separation unit 20.

The crude product fed to light ends column 18 via lines 54, 56 has much reduced levels of methyl iodide, methyl acetate and/or dimethyl ether as compared with a conventional carbonylation system because the methyl acetate and/or dimethyl ether has been consumed in the pre-flasher/post reactor vessel 14 and the methyl iodide and optionally methyl acetate and/or dimethyl ether have been pre-flashed, to low pressure vent scrubber system 40 as shown in the diagram. From light ends column 18, the product is fed forward in a purified stream 58 with most of the methyl iodide and methyl acetate removed from the product.

Stream 58 is fed forward to an iodine removal system 60 which may include chemical treatment or treatment with an ion exchange resin before being fed forward via line 62 to a separator 64 to separate acetic acid from acetic anhydride. Acetic acid is withdrawn at 66 and may be recycled as a solvent or used as a scrubber fluid, if so desired, or simply taken as product.

Crude acetic anhydride is removed from separator 64 and purified in acetic anhydride purification unit 68 to remove, for example, diacetoxyethane. Finished product is taken at 70.

The overhead from column 18 is condensed and exits via 72 to receiver 74 and may be recycled as is known in the art. Non-condensibles, i.e., at 76 are fed to the low pressure vent scrubbing system, which may utilize methanol and/or acetic acid and/or methyl acetate shown at 78. In this regard, there is provided an absorption tower 80. The scrub fluid in the low pressure scrubber, that is, the spent scrub fluid, may be fed directly to reactor 12 via line 82 as shown in the diagram when methyl acetate, acetic acid, acetic anhydride or mixtures thereof are used as the scrub fluid. Preferably, more than 90% or 95% of the methyl iodide is removed from the vent gas by the absorbent fluid prior to additional processing. The scrubber fluid is generally chilled to a temperature of from about 5° C. to about 25° C. prior to use in the tower, with the proviso that when acetic acid is used as the scrubber solvent, the temperature of the solvent is held at 17° C. or more to prevent freezing.

If methanol and/or acetic acid are used as scrub fluid, the spent fluid may be fed to an esterification tower via dashed line **82*a*** before being returned to the production system, as described below.

There is optionally provided an esterification tower 92 as shown in FIG. 2 for supplying methyl acetate to reactor 12 via line 22. Generally, esterification unit 92 is a reactive distillation system of the class described in U.S. Pat. No. 4,435,595 to Agreda et al., the disclosure of which is incorporated herein by reference. System 92 includes, in general, a reactive distillation column 94 provided with an inlet 96 for acetic acid, a feed port 98 for methanol, as well as a steam supply 100 at the base of the reactor column. Acid catalyst is supplied through a feed line 102, while methyl acetate produced from methanol and acetic acid fed to system 92 is taken overhead in line 103. The product stream is condensed at 104 and split at 106, a portion of the product stream is provided as reflux 108 while additional product is provided to reactor 12 via line 22. By-product water, acid catalyst and excess methanol, if any, are withdrawn from the base of the column through line 110.

Esterification unit 92 may be fed acetic acid from line 66 via line 96 and methanol via line 98. Optionally, acetic acid and/or methanol can be used as the scrub fluid and fed to unit 92 via line 82*a* from absorber/scrubber system 40 shown on FIG. 1 when the esterification unit is appropriately configured. For example, if acetic acid is used as the scrub fluid, spent fluid may be fed via line 82*a* to line 96, while if methanol is used as the scrub fluid, then spent fluid is fed via line 82*a* to port 98.

The non-condensibles, including carbon monoxide from tower 80 exit via line 84 and may be further purified by pressure swing adsorption or vacuum swing adsorption equipment or a membrane separation unit included in the scrubber/absorber system 40 as is known in the art and indicated on FIG. 1. In this regard, there is provided description of these processes and equipment in U.S. Pat. No. 5,529,970 to Peng and U.S. Pat. No. 6,322,612 to Sircar et al., the disclosures of which are incorporated herein by reference.

In a preferred embodiment, recovered carbon monoxide is re-compressed and fed to the reactor via line 24, for example.

From catalyst separation unit 20, catalyst is recycled via line 86 to a catalyst work-up unit 88 where waste polymer and corrosion products are removed. Reconditioned catalyst is supplied via line 90 to reactor 12.

A high pressure absorber is not required in the embodiment illustrated in FIG. 1, saving capital and operating costs. In other embodiments, use of a high pressure absorber can be minimized, reducing operating costs.

It will be appreciated from the foregoing that lower methyl iodide and methyl acetate and/or dimethyl ether levels in the resulting flashed crude product stream 46, 56 debottlenecks the light ends column. High gas sparge rates can be achieved without losing carbon monoxide because of carbon monoxide consumption in pre-flasher/post reactor 14.

Carbonylation system 10 may be modified to utilize various operating configurations, equipment, catalysts or feedstocks as are known in the art. See, for example, *Applied Homogeneous Catalysis With Organometallic Compounds*, Cornils, B. and Herrmann, W., Ed. Bench Edition, Chapter 2, pp. 116-131, Wiley (Weinheim 2000), the disclosure of which is incorporated herein by reference. See, also, U.S. Pat. No. 4,374,070, issued Feb. 15, 1983, entitled "Preparation of Acetic Anhydride", to Larkins et al; U.S. Pat. No. 4,333,884, issued Jun. 8, 1982, entitled "Production of Acetic Anhydride", to Kübbeler; United States Patent Application Publication No. US 2007/0287862, published Dec. 13, 2007, entitled "Production of Acetic Acid and Mixtures of Acetic Acid and Acetic Anhydride", of Kline et al.; and European Patent Application Publication No. 0 087 870, published Sep. 7, 1983, entitled "Process for the Production of Acetic Anhydride and Acetic Acid", of Cooper, the disclosures of which are also incorporated herein by reference.

A Group VIII catalyst metal used in connection with the present invention is typically a rhodium catalyst. The selection of catalyst is not critical to the operation of the present invention. In the event that a rhodium-based catalyst is selected, the rhodium metal catalyst may be added in any suitable form such that rhodium is in the catalyst solution as an equilibrium mixture including $[Rh(CO)_2I_2]^-$ anion, as is well known in the art.

Iodide salt stabilizer/co-promoters used in connection with this invention may be in the form of a soluble salt of an alkali metal or alkaline earth metal or a quaternary ammonium or phosphonium salt. In certain embodiments, the catalyst stabilizer/co-promoter is lithium iodide, lithium acetate, or mixtures thereof. The iodide salt may be added as a mixture of salts such as a mixture of lithium iodide and sodium iodide and/or potassium iodide. Alternatively, the iodide salt stabilizer/co-promoter may be added as a salt precursor which generates iodide anion in-situ under the operating conditions of the reaction system. A wide range of non-iodide salts which are useful as precursors include alkali metal acetates and carboxylates which will react with methyl iodide and/or HI to generate the corresponding iodide salt stabilizer. Suitable iodide salts may likewise be generated in situ from non-ionic precursors, such as a phosphine oxide, arsenes, phosphines, amines, amino acids, sulfides, sulfoxides or any suitable organic ligand or ligands if so desired. Phosphine oxides, phosphines, amines, amino acids or other nitrogen or phosphorous containing compounds and suitable organic ligands generally undergo quaternization in the presence of methyl iodide at elevated temperatures to yield salts which maintain elevated iodide anion concentration in the reaction mixture. The iodide salt stabilizer/co-promoters are thus defined by their ability to maintain elevated iodide anion levels, rather than by the form in which they are added to the system. One way of introducing iodide salt co-promoters is by incorporating suitable moieties into a rhodium catalyst system or complex as cations or ligands (typically monodentate or bidentate ligands) associated with rhodium added to the reaction mixture. Under carbonylation conditions in the presence of methyl iodide, these complexes decompose and/or quaternize to provide elevated levels of iodide anions. In this regard, the following Chinese References are of particular interest: Chinese Publication CN1345631; Application No. 00124639.9; Chinese Publication No. CN1105603; Application No. 94100505.4; and Chinese Publication No. CN1349855; Application No. 00130033.4. Suitable rhodium catalyst complexes which provide iodide salt co-promoter thus include complexes having the following structures:

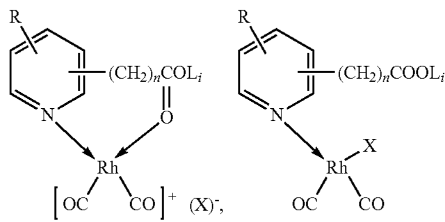

wherein R is H, or a carboxyl-containing hydrocarbon derivative; $(X^-)$ is $BPh_4^-$, $BF_4^-$, or $CH_3COO^-$; X is I, Cl, or Br; and n=0, 1, or 2. Other compounds useful as iodide salt co-promoters include pyridine derivatives such as:

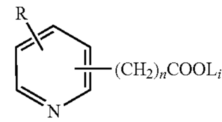

wherein R is H, or a carboxyl-containing hydrocarbon derivative, and n is 0, 1, or 2. Preferably, R is H, or e.g., lithium pyridine-2-formate, lithium pyridine-3-formate, lithium pyridine-4-formate, lithium pyridine-2-acetate, lithium pyridine-3-acetate, lithium pyridine-4-acetate, or lithium pyridine-3-propionate.

Group VA oxides which decompose under carbonylation conditions to yield quaternary iodide salts which may likewise be employed as stabilizers. Specific examples of pentavalent Group VA oxides that can be used include, but are not limited to, triethylphosphine oxide, tributylphosphine oxide, tripentylphosphine oxide, diphenylmethylphosphine oxide and triphenylphosphine oxide, or mixtures of these compounds. Further description is provided in U.S. Pat. Nos. 6,031,129 and 5,817,869 to Hinnenkamp et al., the disclosures of which are incorporated herein by reference.

One of skill in the art will appreciate that a great many other components may be used as iodide salt co-promoters, or iodide salt precursors; that is, the promoter component of the catalyst system may be (1) an inorganic iodide salt such as lithium iodide and related compounds as noted above or an iodide salt of a quaternary organophosphorus or organonitrogen compound or (2) an inorganic compound or an organophosphorus or organonitrogen compound which forms an iodide salt in the carbonylation zone. The organophosphorus or organonitrogen iodides may be selected from phosphonium iodides, ammonium iodides and heterocyclic aromatic compounds in which at least one ring hetero atom is a quaternary nitrogen atom. Examples of such phosphorus- and nitrogen-containing iodides include, without limitation, tetra(hydrocarbyl)phosphonium iodides such as tributyl(methyl)phosphonium iodide, tetrabutylphosphonium iodide, tetraoctylphosphonium iodide, triphenyl(methyl)phosphonium iodide, tetraphenylphosphonium iodide and the like; tetra(hydrocarbyl)ammonium iodides such as tetrabutylammonium iodide and tributyl(methyl)ammonium iodide; and heterocyclic aromatic compounds such as N-methylpyridinium iodide, N,N'-dimethylimidazolium iodide, N-methyl-3-picolinium iodide, N-methyl-2,4-litidinium iodide, N-methyl-2,4-lutidinium iodide and N-methylquinolinium iodide. The preferred iodide salt promoters comprise alkali metal iodide, e.g, lithium and sodium iodide, and tetraalkylphosphonium iodides, triphenyl(alkyl)phosphonium iodides, tetraalkylammonium iodides and N,N'-dialkylimid-azolium iodides wherein the alkyl groups contain up to 8 carbon atoms.

Methyl iodide is typically also used as reaction mixture component and a promoter; typically combined with a salt stabilizer/co-promoter compound in the catalyst system, especially in connection with rhodium catalyzed systems. These promoters may include salts of a metal of Group IA or Group IIA, or a quaternary ammonium or phosphonium salt or their precursors as described above. Particularly preferred are iodide or acetate salts, e.g., lithium iodide or lithium acetate.

Still other promoters and co-promoters may be used as part of the catalytic system of the present invention as described in European Patent Publication EP 0 849 248, the disclosure of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. A promoter may be present in an effective amount up to the limit of its solubility in the liquid reaction composition and/or any liquid process streams recycled to the carbonylation reactor.

The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 Bar partial pressure, as its presence may result in the formation of hydrogenation products. The partial pressure of carbon monoxide in the reaction is suitably in the range 1 to 70 bar, preferably 1 to 35 bar, and most preferably 1 to 15 bar.

Acetic acid is typically included in the reaction mixture as the solvent for the reaction.

Carbonylatable feedstocks include methyl acetate and dimethyl ether. The present invention may be practiced utilizing a methyl acetate by-product stream from polyvinyl alcohol or polyvinyl alcohol copolymer production processes, if so desired, as described in U.S. Pat. No. 7,115,772 to Picard et al., entitled "Integrated Process for Producing Carbonylation Acetic Acid, Acetic Anhydride, or Coproduction of Each from a Methyl Acetate By-Product Stream", the disclosure of which is incorporated herein by reference. The methyl acetate by-product stream may be purified, if so desired, prior to being fed to the reactor or fed directly in crude by-product form.

Feed to the reactor also optionally includes minor amounts of water and/or methanol or reactive derivatives thereof in addition to methyl iodide, dimethyl ether and methyl acetate. Suitable additional reactive derivatives of methanol include methyl formate, for example. The carbonylation process in the primary reactor and pre-flash/post reactor vessel may be operated on a batch or semi-continuous basis, but preferably in a continuous mode.

The pressure of the carbonylation reaction in the primary reactor is generally in the range 145 psi to 2900 psi (10 to 200 bar), preferably 145 psi to 1450 psi (10 to 100 bar), most preferably 217 psi to 725 psi (15 to 50 bar), for example about 400 psi (28 bar). Pressure in the pre-flash/post reactor vessel is reduced in many cases by from 10 to 40% of the primary reactor pressure, corresponding to a pressure reduction of approximately 40 psi. The pre-flash/post reactor vessel generally operates at a pressure of from about 160 psig to about 400 psig. The flash vessel is typically operated at a pressure within the range of about 14 to about 100 psig. The primary and pre-flash/post reactor vessels are operated at comparable temperatures. The temperature of the carbonylation reaction is suitably in the range 212° F. to 572° F. (100 to 300° C.), preferably in the range 302° F. to 428° F. (150 to 220° C.), for example about 370° F. (188° C.). Referring to FIG. 1, suitable pressures and compositions in the various pieces of equipment and streams are as follows:

Equipment

12—carbonylation reaction pressure=300-500 psig, preferably 350-450 psig

14—Preflasher/Post reactor pressure=200-450 psig, preferably 300-400 psig (always lower pressure than reactor 12)

16—Flasher pressure=0-100 psig, preferably 15-45 psig

80—vent scrubber pressure=5 to 500 psig, preferably 5-100 psig, more preferably 10-50 psig Streams

38—comprising MeI, MeAc, CO

36—comprising HAc, Acetic Anhydride, Rh, dissolved gasses ($CO/CO_2$) and lower concentrations of MeAc and MeI than stream 28

30—comprising CO, $H_2$, $CO_2$, $CH_4$

76—comprising non-condensable gasses and MeI

84—comprising primarily non-condensable gasses with lower concentrations of MeI than stream 30

The difference in pressure between the reactor and pre-flasher/post reactor vessel is perhaps most preferably 30-100 psi as measured at vessel outlets.

Description of Preferred Embodiments

Generally, the pre-flasher/post reactor vessel is operated at a pressure of at least 5 psi lower than the pressure of the reactor vessel, more preferably at least 10 psi, at least 15 psi, at least 20 psi, at least 25 psi, or at least 30 psi lower than the pressure of the reactor vessel.

The homogenous rhodium catalyst is usually present in the reaction mixture at a concentration of from 200 ppm rhodium by weight to 5,000 ppm rhodium by weight of the reaction mixture, such as at a concentration of from 400 ppm rhodium by weight to 2,500 ppm rhodium by weight of the reaction mixture.

Carbon monoxide is typically sparged to the pre-flasher/post reactor vessel by way of a vent stream from the reactor and the light ends from the pre-flasher/post reactor vessel are vented to a scrubber/absorber system. The process thus further comprises recovering carbon monoxide in the scrubber/absorber system and recycling the recovered carbon monoxide to the reactor.

In many embodiments, the feedstock comprises methyl acetate which is also present in the reaction mixture and the methyl acetate in the reaction mixture is reduced in the pre-flasher/post reactor vessel to a level at least 15% lower than the concentration of methyl acetate in the reaction mixture in the reaction vessel. More typically, the methyl acetate in the reaction mixture is reduced in the pre-flasher/post reactor vessel to a level at least 30% lower than the concentration of methyl acetate in the reaction mixture in the reaction vessel. Any suitable source for methyl acetate may be used, for example, methyl acetate may be obtained by a process comprising contacting a vinyl acetate based polymer or copolymer with methanol under conditions sufficient to form a polymer or copolymer of vinyl alcohol and methyl acetate by-product and wherein the process further comprises feeding the by-product methyl acetate to the reactor vessel.

When by-product methyl acetate is used, the process may include purifying the by-product methyl acetate prior to feeding the by-product methyl acetate to the reactor vessel.

Another aspect of the invention is directed to a method of coproducing acetic anhydride and acetic acid using generally the procedure noted above.

Still yet another aspect of the invention is a carbonylation system for producing acetic anhydride or a mixture of acetic anhydride and acetic acid comprising: (a) a reactor vessel adapted for carbonylating a feed stock containing methyl acetate and/or dimethyl ether with carbon monoxide in the presence of a rhodium catalyst and methyl iodide in a substantially anhydrous liquid reaction mixture including acetic acid, acetic anhydride, methyl acetate and/or dimethyl ether and methyl iodide, the reactor being operated at a reaction pressure of from 300 psig to 1500 psig; (b) a pre-flasher/post reactor vessel coupled to the reactor adapted to receive liquid reaction mixture forwarded thereto from the reactor, the pre-flasher/post reactor vessel also being coupled to a carbon monoxide source and receiving additional carbon monoxide therefrom; the pre-flasher/post reactor vessel being further characterized in that it is operated at a pressure of from 200 psig to 750 psig, with the proviso that the pressure in the pre-flasher/post reactor vessel is at least 5 psi lower than the pressure in the reactor vessel and wherein the composition and conditions in the pre-flasher/post reactor vessel are such that light ends are provided to a pre-flasher/post reactor vessel vent and a pre-flash mixture which is enriched in acetic anhydride and/or acetic acid and diminished in methyl iodide and methyl acetate as compared with the reaction mixture is formed; (c) a scrubber coupled to the vent of the pre-flasher/post reactor vessel adapted to recover light ends therefrom; (d) a flash vessel coupled to the pre-flasher/post reactor vessel adapted to receive liquid pre-flash mixture forwarded thereto from the pre-flasher/post reactor vessel, the flasher vessel being operated at a pressure substantially lower than the pre-flasher/post reactor vessel pressure, the flash vessel being further adapted to flash a crude product stream from the pre-flash mixture and provide a recycle reaction mixture; (e) a recycle system coupled to the flash vessel and the reactor vessel configured and adapted for returning recycle reaction mixture from the flash vessel to the reactor vessel; and (f) a purification section coupled to the flash vessel adapted to purify the crude product stream. Typically, the pressure in the pre-flasher/post-reactor vessel is at least 25 psi lower than the pressure in the reactor vessel.

Still further improvements include the system further comprising a pressure-reducing valve coupling the vent stream of the reactor vessel and the pre-flasher/post reactor vessel and/or further comprising a pressure-reducing valve coupling the pre-flasher/post reactor vessel and the scrubber and/or further comprising a pressure-reducing valve coupling the pre-flasher/post reactor vessel and the flash vessel. In some cases, the reactor vessel is exclusively vented to the pre-flasher/post reactor vessel and the system is provided with a single, low pressure vent scrubber.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A method of making acetic anhydride or a mixture of acetic anhydride and acetic acid comprising:

(a) catalytically reacting a feedstock containing methyl acetate and/or dimethyl ether with carbon monoxide in the presence of a homogeneous rhodium catalyst and methyl iodide in a reactor vessel which contains a substantially anhydrous liquid reaction mixture including acetic acid, acetic anhydride, methyl acetate and/or dimethyl ether, methyl iodide and the homogeneous catalyst, the reactor vessel being operated at a reactor pressure;

(b) withdrawing reaction mixture from the reaction vessel and feeding the withdrawn reaction mixture along with additional carbon monoxide to a pre-flasher/post reactor vessel operated at a reduced pressure below the reactor vessel pressure;

(c) venting light ends in the pre-flasher/post reactor vessel and concurrently consuming methyl acetate and/or dimethyl ether in the pre-flasher/post reactor vessel to produce a pre-flash mixture which is enriched in acetic anhydride and diminished in methyl iodide and methyl acetate and/or dimethyl ether as compared with the reaction mixture;

(d) withdrawing the pre-flash mixture from the pre-flasher/post reactor vessel and feeding the pre-flash mixture to a flash vessel;

(e) flashing a crude product stream from the pre-flash mixture in a flash vessel operated at a pressure substantially below the pressure of the pre-flasher/post reactor vessel;

(f) recycling post-flash residue from the flash vessel to the reactor vessel; and (g) purifying the crude product stream.

2. The method according to claim 1, wherein the pre-flasher/post reactor vessel is operated at a pressure of at least 5 psi lower than the pressure of the reactor vessel.

3. The method according to claim 1, wherein the pre-flasher/post reactor vessel is operated at a pressure of at least 10 psi lower than the pressure of the reactor vessel.

4. The method according to claim 1, wherein the pre-flasher/post reactor vessel is operated at a pressure of at least 15 psi lower than the pressure of the reactor vessel.

5. The method according to claim 1, wherein the pre-flasher/post reactor vessel is operated at a pressure of at least 20 psi lower than the pressure of the reactor vessel.

6. The method according to claim 1, wherein the pre-flasher/post reactor vessel is operated at a pressure of at least 25 psi lower than the pressure of the reactor vessel.

7. The method according to claim 1, wherein the pre-flasher/post reactor vessel is operated at a pressure of at least 30 psi lower than the pressure of the reactor vessel.

8. The carbonylation process according to claim 1, wherein the homogenous rhodium catalyst is present in the reaction mixture at a concentration of from 200 ppm rhodium by weight to 5,000 ppm rhodium by weight of the reaction mixture.

9. The carbonylation process according to claim 1, wherein the homogenous rhodium catalyst and is present in the reaction mixture at a concentration of from 400 ppm rhodium by weight to 2,500 ppm rhodium by weight of the reaction mixture.

10. The method according to claim 1, wherein carbon monoxide is sparged to the pre-flasher/post reactor vessel by way of a vent stream from the reactor vessel.

11. The method according to claim 1, wherein the light ends from the pre-flasher/post reactor vessel are vented to a scrubber/absorber system.

12. The method according to claim 11, further comprising recovering carbon monoxide in the scrubber/absorber system and recycling the recovered carbon monoxide to the reactor vessel.

13. The method according to claim 1, wherein the feedstock comprises methyl acetate which is also present in the reaction mixture.

14. The method according to claim 13, wherein methyl acetate in the reaction mixture is reduced in the pre-flasher/post reactor vessel to a level at least 15% lower than the concentration of methyl acetate in the reaction mixture in the reactor vessel.

15. The method according to claim 13, wherein methyl acetate in the reaction mixture is reduced in the pre-flasher/post reactor vessel to a level at least 30% lower than the concentration of methyl acetate in the reaction mixture in the reactor vessel.

16. The method according to claim 13, wherein methyl acetate is obtained by a process comprising contacting a vinyl acetate based polymer or copolymer with methanol under conditions sufficient to form a polymer or copolymer of vinyl alcohol and methyl acetate by-product and wherein the process further comprises feeding the by-product methyl acetate to the reactor vessel.

17. The method according to claim 16, further comprising purifying the by-product methyl acetate prior to feeding the by-product methyl acetate to the reactor vessel.

18. A method of coproducing acetic anhydride and acetic acid comprising:

(a) catalytically reacting a feedstock containing methyl acetate and/or dimethyl ether with carbon monoxide in the presence of a homogeneous rhodium catalyst and methyl iodide in a reactor vessel which contains a substantially anhydrous liquid reaction mixture including acetic acid, acetic anhydride, methyl acetate and/or dimethyl ether, methyl iodide and the homogeneous catalyst, the reactor vessel being operated at a reactor pressure;

(b) withdrawing reaction mixture from the reactor vessel and feeding the withdrawn reaction mixture along with additional carbon monoxide to a pre-flasher/post reactor vessel operated at a reduced pressure below the reactor vessel pressure;

(c) venting light ends in the pre-flasher/post reactor vessel and concurrently consuming methyl acetate and/or dimethyl ether in the pre-flasher/post reactor vessel to produce a pre-flash mixture which is enriched in acetic anhydride and/or acetic acid and diminished in methyl iodide and methyl acetate and/or dimethyl ether as compared with the reaction mixture;

(d) withdrawing the pre-flash mixture from the pre-flasher/post reactor vessel and feeding the pre-flash mixture to a flash vessel;

(e) flashing a crude product stream from the pre-flash mixture in a flash vessel operated at a pressure substantially below the pressure of the pre-flasher/post reactor vessel;

(f) recycling post-flash residue from the flash vessel to the reactor vessel; and (g) purifying the crude product stream.

19. A carbonylation system for producing acetic anhydride or a mixture of acetic anhydride and acetic acid comprising:

(a) a reactor vessel adapted for carbonylating a feed stock containing methyl acetate and/or dimethyl ether with carbon monoxide in the presence of a rhodium catalyst and methyl iodide in a substantially anhydrous liquid reaction mixture including acetic acid, acetic anhydride, methyl acetate and/or dimethyl ether and methyl iodide, the reactor being operated at a reaction pressure of from 300 psig to 1500 psig;

(b) a pre-flasher/post reactor vessel coupled to the reactor adapted to receive liquid reaction mixture forwarded thereto from the reactor, the pre-flasher/post reactor vessel also being coupled to a carbon monoxide source and receiving additional carbon monoxide therefrom;

the pre-flasher/post reactor vessel being further characterized in that it is operated at a pressure of from 200 psig to 750 psig, with the proviso that the pressure in the pre-flasher/post reactor vessel is at least 5 psi lower than the pressure in the reactor vessel and wherein the composition and conditions in the pre-flasher/post reactor vessel are such that light ends are provided to a pre-flasher/post reactor vessel vent and a pre-flash mixture which is enriched in acetic anhydride and/or acetic acid and diminished in methyl iodide and methyl acetate as compared with the reaction mixture is formed;

(c) a flash vessel coupled to the pre-flasher/post reactor vessel adapted to receive liquid pre-flash mixture forwarded thereto from the pre-flasher/post reactor vessel, the flash vessel being operated at a pressure substantially lower than the pre-flasher/post reactor vessel pressure, the flash vessel being further adapted to flash a crude product stream from the pre-flash mixture and provide a recycle reaction mixture;

(d) a recycle system coupled to the flash vessel and the reactor vessel configured and adapted for returning recycle reaction mixture from the flash vessel to the reactor vessel; and (e) a purification section coupled to the flash vessel adapted to purify the crude product stream.

20. The system according to claim 19, wherein the pressure in the pre-flasher/post-reactor vessel is at least 25 psi lower than the pressure in the reactor vessel.

* * * * *